(12) United States Patent
Koch et al.

(10) Patent No.: US 7,153,954 B2
(45) Date of Patent: Dec. 26, 2006

(54) METHOD FOR PREPARATION OF LNA PHOSPHORAMIDITES

(75) Inventors: Troels Koch, Copenhagen (DK); Christoph Rosenbohn, Copenhagen (DK); Daniel Sejer Pedersen, Copenhagen (DK)

(73) Assignee: Santaris Pharma A/S, Horsholm (DK)

( * ) Notice: Subject to any disclaimer, the term of this patent is extended or adjusted under 35 U.S.C. 154(b) by 81 days.

(21) Appl. No.: 10/194,950

(22) Filed: Jul. 12, 2002

(65) Prior Publication Data

US 2003/0032794 A1 Feb. 13, 2003

Related U.S. Application Data

(60) Provisional application No. 60/304,876, filed on Jul. 12, 2002.

(51) Int. Cl.
*C07H 21/00* (2006.01)
*C07H 21/02* (2006.01)
*C07H 21/04* (2006.01)

(52) U.S. Cl. .................. 536/25.3; 536/25.34; 536/22.1
(58) Field of Classification Search .............. 536/25.34, 536/25.3, 22.1
See application file for complete search history.

(56) References Cited

U.S. PATENT DOCUMENTS

| 4,415,732 A | 11/1983 | Caruthers et al. ............. 536/27 |
| 6,596,857 B1 * | 7/2003 | Just et al. ................. 536/25.34 |

FOREIGN PATENT DOCUMENTS

| WO | WO 98/16540 | 4/1998 |
| WO | WO 99/14226 | 3/1999 |

OTHER PUBLICATIONS

Obika et al., "2'–O,4'–CMethylene Bridge Nucleic Acid (2',4'–BNA): Synthesis and Triplex–Forming Properties", Bioorganic and Medicinal Chem., 2001, pp. 1001–1011.*
Vargeese et al., "Efficient activation of Nucleoside Phosphoramidites with 4,5–Dicyanoimidazole during Oligonucleotide Synthesis", Nucleic Acid research, vol. 26, no. 4, pp. 1046–1050, 1998.*
Vargeese et al., "Efficient Activation of Nucleoside Phosphoramidites with 4,5–Dicyanoimidazole During Oligonucleoside Synthesis", Nucleic Acid Research, 26(4), pp. 1046–1050, 1998.*
Koshkin et al., "LNA (Locked Nucleic Acids): Synthesis of Adenine, Cytosine, Guanine, 5–Methylcytosine, Thymine, and Uracil Bicyclonucleoside Monomers, Oligermisation, and Unprecedented Nucleic Acid Recognition" Tetrahedron, 54, pp. 3607–3630, 1998.*
B. Dahl et al., *Nucleic Acids Research*, 15(4):72–1729–1743 (1987).
S. Beaucage et al., *Tetrahedron*, 48(12):2223–2311 (1992).
C. Vargeese et al., *Nucleic Acids Research*, 26(4):1046–1050 (1998).
A. Kittaka et al., *Nucleosides & Nucleotides*, 18(11&12):2769–2783 (1999).
A. Kittaka et al., *Synlett*, S1:869–872 (1999).
A. Koshkin et al., *Tetrahedron*, 54:3607–3630 (1998).
A. Hakansson et al., *J. Org. Chem.*, 65:5161–5166 (2000).
S. Obika et al., *Bioorganic & Medicinal Chemistry*, 9:1001–1011 (2001).
S. Obika et al., *Angew. Chem. Int. Ed.*40(11):2079–2081 (2001).
S. Hamamoto et al., *Chem. Lett.*, 8:1401–1404 (1986).
Leuck et al., Abstract of Poster presented at 4th Winter Conference on Medicinal and Bioorganic Chemistry, Jan. 28–Feb. 2, 2001.*
Poster presented at 4th Winter Conference on Medicinal and Bioorganic Chinstry, Jan. 28–Feb. 2, 2001.
Abstract of Poster presented at 4th Winter Conference on Medicinal and Bioorganic Chemistry, Jan. 28 –Feb. 2, 2001.

\* cited by examiner

*Primary Examiner*—Shaojia Anna Jiang
*Assistant Examiner*—Traviss C McIntosh, III
(74) *Attorney, Agent, or Firm*—Peter F. Corless; Christine C. O'Day; Edwards Angell Palmer & Dodge LLP

(57) ABSTRACT

The present invention relates to large scale preparation of LNA phosphoramidites using a 2-cyanoethyl-N,N,N',N'-tetra-substituted phosphoramidite and a nucleophilic activator, e.g. 2-cyanoethyl-N,N,N',N'-tetraisopropylphosphoramidite and 4,5-dicyanoimidazole. The method is faster and more cost efficient that previously known methods.

7 Claims, 3 Drawing Sheets

METHOD FOR PREPARATION OF LNA PHOSPHORAMIDITES

The present application claims the benefit of U.S. provisional application No. 60/304,876, filed 12 Jul. 2002, which is incorporated herein by reference in its entirety.

FIELD OF THE INVENTION

The present invention relates to a high yielding, fast method for large-scale LNA phosphoramidites synthesis.

BACKGROUND OF THE INVENTION

Locked Nucleic Acid (LNA) monomers and oligonucleotides were invented in 1997 (WO9914226) and have showed promising results as antisense drug candidates. However, there is no production method described in the literature for large scale LNA-phosphoramidite synthesis providing optimal yields of the LNA amidites necessary for efficient preparation of LNA based antisense drugs.

Oligonucleotide synthesis is typically performed using the phosphoramidite method, invented by Caruthers, U.S. Pat. No. 4,415,732, in 1980 and improved a couple of years later by Köster U.S. Pat. No. 4,725,677. LNA oligomers are being synthesised according to the phosphoramidite method, but so far the large scale supply of LNA monomers has been a problem due to slow reactions, side product formation during the reaction and reagents unstable at room temperature have been employed.

The mechanism of phosphoramidite activation and coupling in oligonucleotide syntheses has been studied in detail. Traditionally tetrazole has been used (Dahl et al. 1987, *Nucleic Acid Research*, 15, 1729–1743; Beaucage & Iver, 1992, *Tetrahedron*, 48, 2223–2311). The proposed mechanism of tetrazole is two step, first tetrazole protonates trivalent phosphorous followed by displacement of the N,N-diisopropylamine by the tetrazolide. This latter intermediate is very reactive with hydroxynucleophiles such as 5'-OH on nucleic acids. Therefore, tetrazole acts both as acid and as nucleophilic agent.

Vargeese et al. (Vargeese, C.; Carter, J.; Krivjansky, S.; Settle, A.; Kropp, E.; Peterson, K.; Pieken, W. *Nucleic Acid Research*, 1998, 26, 1046–1050; WO9816540;) have described an activator for the coupling of phosphoramidites to the 5'-hydroxyl group during oligonucleotide synthesis. The activator is 4,5-dicyanoimidazole (DCI) and its effectiveness is thought to be based on its nucleophilicity. It was shown that DCI significantly increased the yield in phosphoramidite oligomerisation.

Vargeese et al. has described a method of small scale DNA phosphoramidite thymine monomer synthesis using DCI, but the method they used provided a moderate yield (75%) after several re-precipitations of the amidite. Kittaka et al. (Kittaka A., Kuze T.; Amano M.; Tanaka H.; Miyasaka T.; Hirose K.; Yoshida T.; Sarai A.; Yasukawa T. and Ishii S. *Nucleosides & Nucleotides* 18, 2769–2783, 1999) have also used DCI for amidite synthesis but they reported an even lower yield of the product (65%). Kittaka et al. (Kittaka A.; Horii C.; Kuze T.; Asakura T.; Ito K.; Nakamura K. T.; Miyasaka T. and Inoue J., *Synthetic letters*, S1, 869–872, 1999) have also made a derivatised uridine phosphoramidite by 3'-O phosphitylation using DCI (0.7 eq), but without describing the reaction parameters further. The yield was reported to be 92%. Generally, phosphitylation of uracil and thymine provide the highest yields because these nucleobases usually do not interfere with the phosphitylation reagents.

Accordingly, there is nothing in the literature describing that DCI has been used as an activator for LNA phosphoramidite synthesis.

The previously reported oxy-β-D-ribo-LNA (FIG. 2) method of synthesis used 2-cyanoethyl-N,N-diisopropylchlorophosphoramidite and diisopropylethylamine (Koshkin, A. A.; Singh, S. K.; Nielsen, P.; Rajwanshi, V. K.; Kumar, R.; Meldgaard, M.; Olsen, C. E.; Wengel, *J. Tet.* 1998, 54, 3607–3630). The reported yields were low (LNA-T 70%, LNA-U 58%, LNA-G 64%, LNA-A 73% and no yield for LNA-C was reported). The previously reported method for synthesising the oxy-α-L-ribo thymine phosphoramidite (FIG. 3) also utilized 2-cyanoethyl-N,N-diisopropylchlorophosphoramidite and diisopropylethylamine and gave a yield of 60% (Hakansson, A. E.; Koshkin, A. A.; Sorensen M. D.; Wengel J. *J.Org.Chem.* 2000, 65, 5161–5166).

SUMMARY OF THE INVENTION

The present invention provides a novel high yielding and fast method for the large scale synthesis of pure LNA phosphoramidites. In the production of LNA monomers as phosphoramidites, the phosphitylation step is crucial. If necessary also a facile and efficient purification is desired, due to the reactivity of the phosphoramidites, so as to avoid their decomposition during purification. An absolute purity of the amidites is a prerequisite because the monomers are used in long sequential oligomerisations over some time where also impurities can cause the decomposition of the phosphoramidites.

Figure 3:
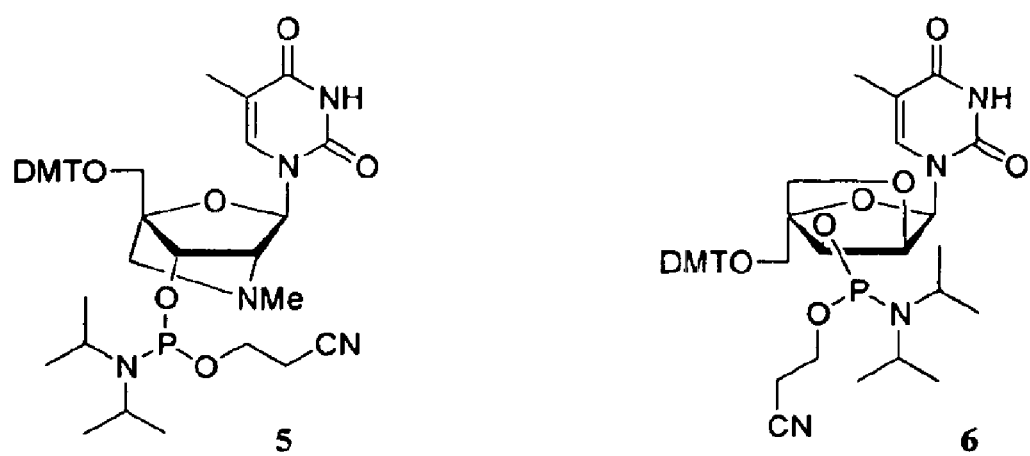
FIG. 3: Amine-β-D-ribo-LNA phosphoramidites and oxy-α-L-ribo-LNA thymine phosphoramidite.

The novel strategy is demonstrated by the synthesis of oxy-β-ribo-LNA phosphoramidites where B is $A^{Bz}$, $^{Me}C^{Bz}$, $G^{iBu}$ and T and oxy α-L-ribo-LNA-T (FIG. 3).

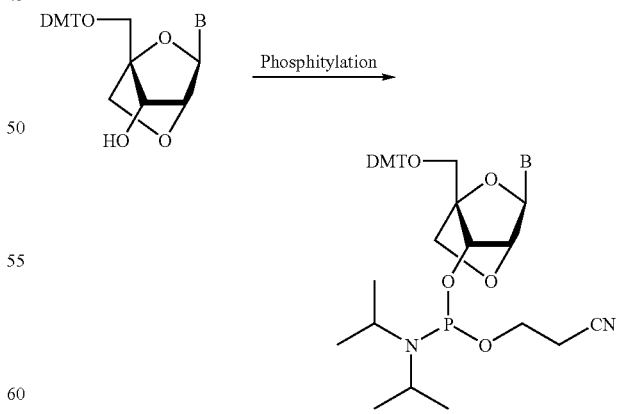

The present invention provides a method for the synthesis of an LNA phosphoramidite, the method comprising phosphitylation of the 3'-OH groups of an LNA monomer with a 2-cyanoethyl-N,N,N',N'-tetra-substituted phosphoramidite in the presence of a nucleophilic activator.

The advantages of the present activation method is:
a) Easy handling
b) All reagents are stabile at room temperature
c) Only 0.7 equivalents DCI are necessary
d) Easy workup
e) Fast and high yielding reaction at room temperature
f) Cost efficient reaction
g) Chromatography not essential for obtaining amidites of high purity The known phosphitylation side reaction of the guanine nucleobase followed by slow transfer/rearrangement to give the desired amidite (Nielsen, J.; Taagaard, M.; Marugg, J. E.; van Boom, J. H.; Dahl, O. *Nuc.Acid.Res.* 1986, 14, 7391–7403) (see FIG. 1) was not observed using the conditions according to the present invention.

DETAILED DESCRIPTION OF THE INVENTION

As used herein, the term "LNA monomer" refers to a ribonucleotide having a 2',4'-bridge (in particular a —O—CH$_2$— (oxy-LNA), —S—CH$_2$— (thio-LNA), —NR—CH$_2$— (amino-LNA, R being hydrogen, C$_{1-6}$-alkyl, phenyl, benzyl, etc.) bridge) as described in the International Patent Application WO9914226 and subsequent WO0056746, WO0056748, WO0066604 and WO0228875.

Particularly interesting examples of LNA monomers of are those referred to as oxy-β-D-ribo-LNA (cf. FIG. 2), thio-β-D-ribo-LNA, amino-β-D-ribo-LNA, oxy-α-L-ribo-LNA (cf. FIG. 3), thio-α-L-ribo-LNA or amino-α-L-ribo-LNA.

Figure 2:
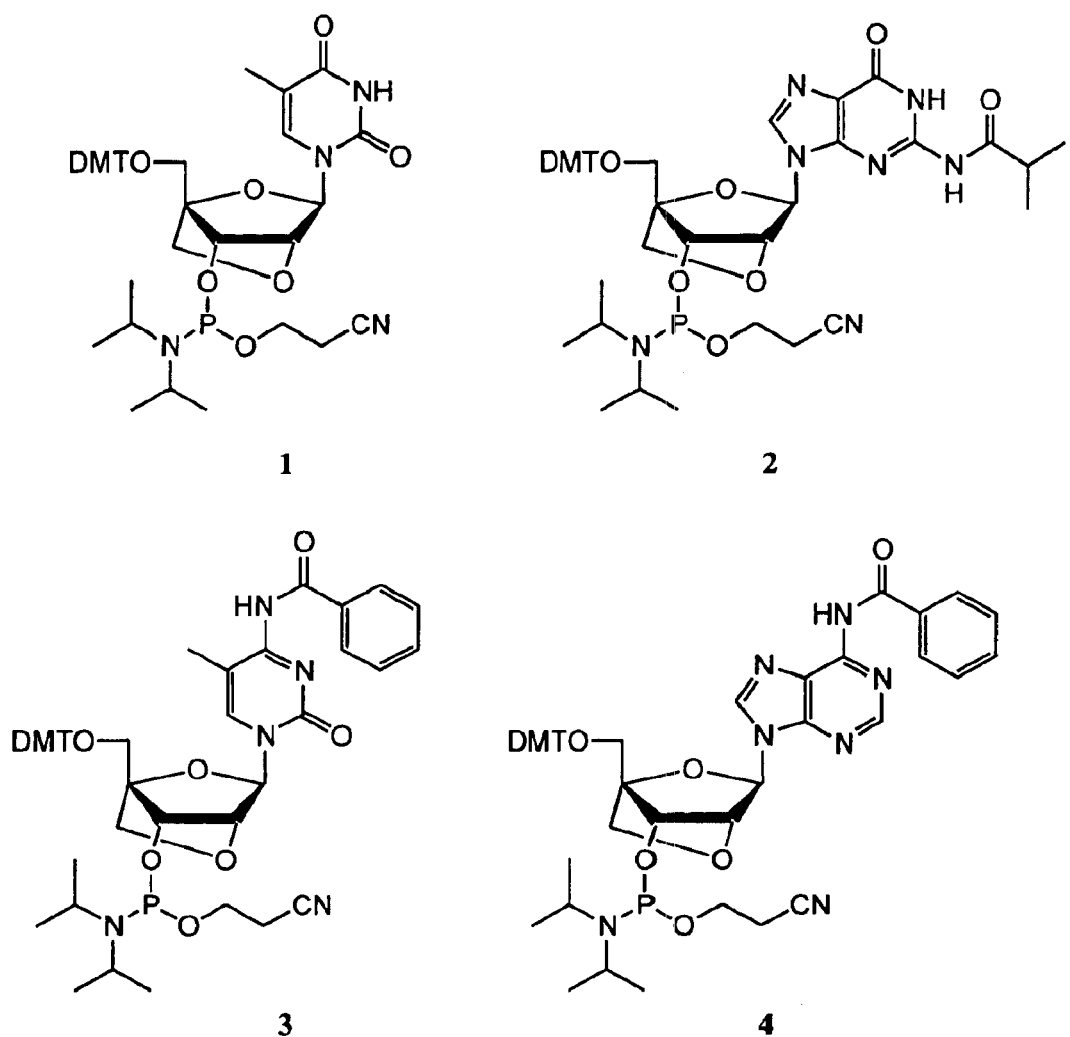
FIG. 2: Oxy-β-D-ribo-LNA phosphoramidites.

As used herein, the term "LNA phosphoramidite" refers to a nucleotide with a protected 5'-hydroxy group (e.g. DMT protected as illustrated in FIGS. 2 and 3), in which the 3'-hydroxy group is coupled to a trivalent phosphorous atom, which in turn is bonded to a suitable leaving group such as a N,N-dialkylamine, e.g. diisopropylamine and a protecting group such as the cyanoethyl (NCCH$_2$CH$_2$—) group. Any LNA phosphoramidite that can be used in solid or liquid phase oligonucleotide synthesis can be used in the present invention, including protected dimer and trimer LNA phosphoramidite.

As used herein, the term "2-cyanoethyl-N,N,N',N'-tetrasubstituted phosphoramidite", also referred to as "PN$_2$-reagent", refers in short to a 2-cyanoethyl-N,N,N',N'-tetrasubstituted phosphoramidite, wherein the term "substituted" means a linear, cyclic or branched unsaturated hydrocarbon such as allyl or vinyl or saturated hydrocarbon or substituted hydrocarbon group or aromatic group or substituted aromatic group having 1 to 9 carbon atoms, such as methyl, ethyl, propyl, iso-propyl, pentyl, cyclopentyl, hexyl, cyclohexyl, preferred examples alkyl are methyl, ethyl, propyl, iso-propyl, butyl, tert-butyl, iso-butyl, pentyl, cyclopentyl, hexyl, cyclohexyl, in particular methyl, ethyl, propyl, iso-propyl, tert-butyl, iso-butyl, cyclohexyl, propylene, butylene, pentylene, hexylene, heptylene, where the substituents can be a hetroatom such as oxygen or nitrogen.

The LNA monomer as well as the phosphoramidite LNA monomer may carry any nucleobase in the 1' position.

In the present context, the term "nucleobase" covers naturally occurring nucleobases as well as non-naturally occurring nucleobases. It should be clear to the person skilled in the art that various nucleobases which previously have been considered "non-naturally occurring" have subsequently been found in nature. Thus, "nucleobase" includes not only the known purine and pyrimidine heterocycles, but also heterocyclic analogues and tautomers thereof. Illustrative examples of nucleobases are adenine, guanine, thymine, cytosine, uracil, purine, xanthine, diaminopurine, 8-oxo-N$^6$-methyladenine, 7-deazaxanthine, 7-deazaguanine, N$^4$,N$^4$-ethanocytosin, N$^6$,N$^6$-ethano-2,6-diaminopurine, 5-methylcytosine, 5-(C$^3$–C$^6$)-alkynylcytosine, 5-fluorouracil, 5-bromouracil, pseudoisocytosine, 2-hydroxy-5-methyl-4-triazolopyridin, isocytosine, isoguanin, inosine, N$^6$-alylpurines, N$^6$-acylpurines, N$^6$-benzylpurine, N$^6$-halopurine, N$^6$-vinylpurine, N$^6$-acetylenic purine, N$^6$-acyl purine, N$^6$-hydroxyalkyl purine, N$^6$-thioalkyl purine, N$^2$-alkylpurines, N$^4$-alkylpyrimidines, N$^4$-acylpyrimidines, N$^4$-benzylpurine, N$^4$-halopyrimidines, N$^4$-vinylpyrimidines, N$^4$-acetylenic pyrimidines, N$^4$-acyl pyrimidines, N$^4$-hydroxyalkyl pyrimidines, N$^6$-thioalkyl pyrimidines, thymine, cytosine, 6-azapyrimidine, including 6-azacytosine, 2- and/or 4-mercaptopyrimidine, uracil, C$^5$-alkylpyrimidines, C$^5$-benzylpyrimidines, C$^5$-halopyrimidines, C$^5$-vinylpyrimidine, C$^5$-acetylenic pyrimidine, C$^5$-acyl pyrimidine, C$^5$-hydroxyalkyl purine, C$^5$-amidopyrimidine, C$^5$-cyanopyrimidine, C$^5$-nitropyrimidine, C$^5$-aminopyrimdine, N$^2$-alkylpurines, N$_2$-alkyl-6-thiopurines, 5-azacytidinyl, 5-azauracilyl, trazolopyridinyl, imidazolopyridinyl, pyrrolopyrimidinyl, and pyrazolopyrimidinyl. Functional oxygen and nitrogen groups on the base can be protected as necessary or desired. Suitable protecting groups are well known to those skilled in the art, and included trimethylsilyl, dimethylhexylsilyl, t-butyldimethylsilyl, and t-butyidiphenylsilyl, trityl, alkyl groups, acyl groups such as acetyl and propionyl, methanesulfonyl, and p-toluenesulfonyl, imines such as N-dimethylmethyleneeneamine and dibutylmethyleneeneamine. Preferred bases include cytosine, methyl cytosine, uracil, thymine, adenine and guanine.

LNA phosphoramidites according to the present invention are prepared in high yield with 2-cyanoethyl-N,N,N',N'-tetraisopropylphosphoramidite (a PN$_2$-reagent). This reagent has not successfully been used to prepare LNA phosphoramidites before. Previously 2-cyanoethyl-N,N-diisopropylchlorophosphoramidite has been used for preparation of LNA amidites. This has not afforded the high purity, high yields and low reaction times according to the present invention.

The surprising finding in the present inventions is that 2-cyanoethyl-N,N,N',N'-tetraisopropylphosphoramidite can be activated by 4,5-dicyanoimidazole and that this complex provides the accurate reactivity, during the conditions described, to secure efficient phosphitylation of all 4 LNA DMT-protected nucleosides including the G-nucleoside. With the previous known methods using 2-cyanoethyl-N,N-diisopropylchlorophosphoramidite the phosphitylation reaction would proceed via oxygen on the protected guanine nucleobases (FIG. 1a) and thereafter be rearranged to the thermodynamically stable 3'-O-amidite (FIG. 1b). The disadvantages with the previous method were that the final product contained side products and that it required significantly longer reaction time, (up to 24 h) due to the slow rearrangement resulting in the thermodynamical product.

The traditional procedures for making LNA phosphoramidites provided yields ranging from 14–73%, whereas the present procedure provides yields of 95% or higher. This is also remarkable for the reason that the corresponding reaction for DNA/RNA nucleotides only provides yields of 92%.

Another advantage of the present invention is that the reactions are finished in 0.5–4 hours, preferably 1.0–3.5 hours, and that chromatography of the LNA amidites is unnecessary due to the efficient reaction. Thus, the phosphitylation reaction is typically allowed to proceed for 0.1–12 hours, such as 0.2–8 hours, e.g. 0.5–4.0 hours, such as 1.0–3.5 hours.

An LNA phosphoramidite for direct use in oligonucleotide synthesis may be obtained directly or by simple precipitation of the product from the reaction mixture. Thus, in a particular aspect of the invention, the method comprises at the most one precipitation step.

Suitable nucleophilic activators for use in the present invention include, but are not limited to, 4,5-dicyanoimidazole (DCI), 4-alkylthioimidazole, 2-alkylthioimidazole, 2-nitroimidazole, 4-nitroimidazole, 4,5-dihaloimidazole, 4-haloimidazole, 2-haloimidazole and 5-alkoxytetrazole. DCI is the preferred nucleophilic activator. DCI has a $pK_a$ of 5.2 and is easily dissolved in acetonitrile.

Suitable $PN_2$.reagents are for example, but not limited to, 2-cyanoethyl-N,N,N',N'-tetraisopropylphosphoramidite and 2-cyanoethyl-N,N,N',N'-tetraethylphosphoramidite and the reagents described by Dahl, B. H., Nielsen J. and Dahl O. *Nucleic Acid Research,* 1987, 15, 1729–1743 all incorporated here by reference. It is presently believed that 2-cyanoethyl-N,N,N',N'-tetraisopropylphosphoramidite and 2-cyanoethyl-N,N,N',N'-tetraethylphosphoramidite are especially relevant, in particular 2-cyanoethyl-N,N,N',N'-tetraisopropylphosphoramidite.

A currently preferred combination is where the 2-cyanoethyl-N,N,N',N'-tetra-substituted phosphoramidite is the 2-cyanoethyl-N,N,N',N'-tetraisopropylphosphoramidite and the nucleophilic activator is 4,5-dicyanoimidazole.

The molar ratio between the LNA monomer and the nucleophilic activator is typically in the range of 1:0.0001 to 1:10, preferably 1:0.0001 to 1:1, and more preferably 1:0.0001 to 1:0.7.

The molar ratio between the LNA monomer and the $PN_2$-reagent is typically in the range of 1:0.9 to 1:10, preferably 1:0.95 to 1:5, more preferably 1:1.

The currently most interesting LNA monomers are those which have a nucleobase selected from guanine, thymine, cytosine, methyl cytosine, uracil and adenine, typically in the protected from such as N-benzoyl protected cytosine ($C^{Bz}$), N-benzoyl protected methyl cytosine ($^{Me}C^{Bz}$), N-isobutanoyl protected guanine ($G^{Ibu}$), uracil (U), thymine (T), N-benzoyl protected adenine ($A^{Bz}$).

EXAMPLES

Example 1

Phosphitylation Methods

Four phosphitylation methods was examined and compared:

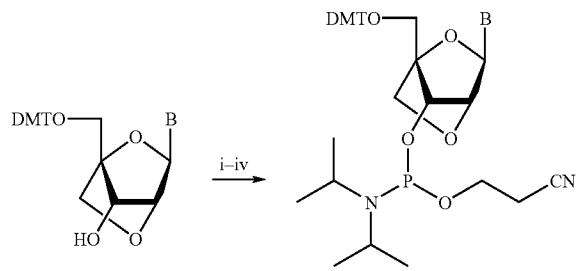

Figure 1:
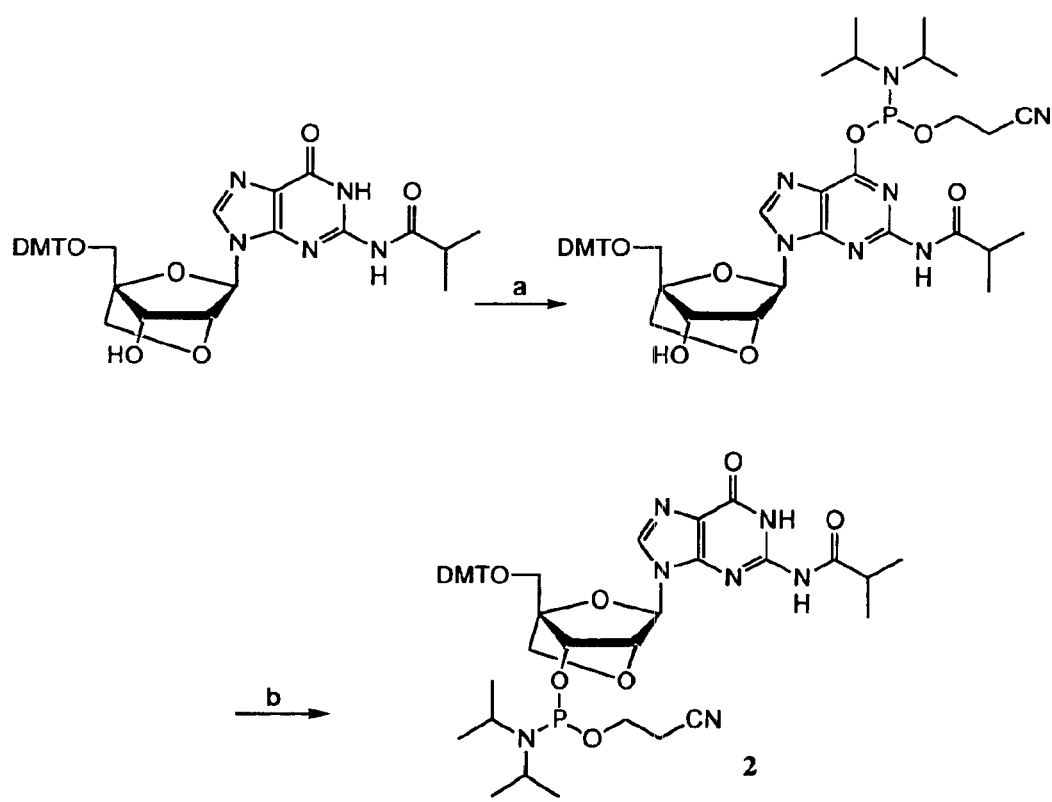
FIG. 1: Phosphitylation of guanine, a) 2-Cyanoethyl-N,N-diisopropylchlorophosphoramidite, diisopropylethylamine, b) Phosphitylation of guanine 3'OH via the transfer/rearrangement reaction (slow).

Phosphitylation reaction. B=$A^{Bz}$, $C^{Bz}$, $^{Me}C^{Bz}$, $G^{Ibu}$ and T i. 2-Cyanoethyl-N,N-diisopropylchlorophosphoramidite, diisopropylethylamine ii. 2-Cyanoethyl-N,N,N', N'-tetraisopropylphosphoramidite, 1H-tetrazole iii. 2-Cyanoethyl-N,N,N',N'-tetraisopropylphosphoramidite, pyridinium trifluoroacetate iv. 2-Cyanoethyl-N,N,N',N'-tetraisopropylphosphoramidite, 4,5-dicyanoimidazole 2-Cyanoethyl-N,N-diisopropylchlorophosphoramidite appeared to have several disadvantages compared to 2-cyanoethyl-N,N,N',N'-tetraisopropylphosphoramidite ($PN_2$-reagent). It is unstable at room temperature, expensive and difficult to handle due to its high reactivity. Furthermore undesired reactions with the nucleobases are often observed with 2-cyanoethyl-N,N-diisopropylchlorophosphoramidite (FIG. 1).

Three different activators (1H-tetrazole, pyridinium trifluoroacetate and 4,5-dicyanoimidazole) were investigated with 2-cyanoethyl-N,N,N',N'-tetraisopropylphosphoramidite. 4,5-Dicyanoimidazole (DCI) gave the best results.

Example 2

General Experimental Procedure for the Preparation of LNA Phosphoramidites 1–6

A 0.2 M solution of the LNA nucleoside (1.0 equiv) in anhyd $CH_2Cl_2$ was stirred under argon. A 1.0 M solution of DCI (0.70 equiv) in anhyd MeCN was added followed by drop wise addition of 2-cyanoethyl-N,N,N',N'-tetraisopropylphosphorodiamidite (1.0 equiv). When the reaction was completed (monitored by analytical TLC*) it was diluted with $CH_2Cl_2$ and washed twice with sat. aq $NaHCO_3$ and once with brine. The organic phase was dried ($Na_2SO_4$), filtered and concentrated in vacou to give a colourless foam. All phosphoramidites were isolated in very high yields ($\geq 95\%$). No by-products could be detected by HPLC-MS, TLC or $^{31}$P-NMR (purity≈100%). If starting materials are dry and pure chromatography is not necessary.
*All phosphitylation reactions were completed in less than 2 h except for the G phosphoramidite (2) synthesis taking up to 4 h to be completed.

Synthesis of (1R,3R,4R,7S)-3-(4-N-Benzoyl-5-methylcytosin-1-yl)-7-(2-cyanoethoxy-(diisopropylamino)phosphinoxy)-1-(4,4'-dimethoxytrityloxymethyl)-2,5-dioxabicyclo[2.2.1] heptane (3)

(1R,3R,4R,7S)-3-(4-N-Benzoyl-5-methylcytosin-1-yl)-1-(4,4'-dimethoxytrityloxymethyl)-7-hydroxy-2,5-dioxabicyclo[2.2.1]heptane (4.86 g, 7.2 mmol) was dissolved in anhyd $CH_2Cl_2$ (40 mL) and 4,5-dicyanoimidazole in MeCN (1.0 M, 5 mL) was added. Stirred at ambient temperature under argon. 2-Cyanoethyl-N,N,N',N'-tetraisopropylphosphorodiamidite (2.4 ml, 7.2 mmol) was added drop wise to the reaction mixture. After 2 h the reaction was diluted with $CH_2Cl_2$ (100 mL) and transferred to a separation funnel and extracted with sat. aq. $NaHCO_3$ (2×150 mL) and brine (150 mL). The combined aqueous phases were extracted with $CH_2Cl_2$ (100 mL). The organic phases were pooled and dried ($Na_2SO_4$). After filtration the organic phase was evaporated in vacou to give a slightly yellow foam (6.0 g, 95% yield). A small sample was removed for comparison with the chromatographed material. The product was purified by Dry Column Vacuum Chromatography (Ø10 cm; Silica pretreated with 5% $Et_3N$ in n-heptane v/v; 0→70% EtOAc, n-heptane v/v). Selected fractions containing 3 were combined and evaporated in vacou to give a colourless foam (5.3 g, 84% yield).

No difference in coupling efficiency could be detected on the oligonucleotide synthesiser in a coupling efficiency assay (vide supra) between the crude and chromatographed phosphoramidite.

The compounds 1, 2, 4, 5 and 6 were prepared in a similar manner.

Analytical Data for Phosphoramidites 1–6.

(1R,3R,4R,7S)-7-(2-Cyanoethoxy (diisopropylamino)phosphinoxy)-1-(4,4'-dimethoxytrityloxymethyl)-3-(thymin-1-yl)-2,5-dioxabicyclo[2:2:1]heptane (1)

$^{31}$P-NMR (CDCl$_3$, 121.49 MHz): δ 150.0 (s), 149.3 (s). MS (ES): m/z calcd for C$_{41}$H$_{49}$N$_4$O$_9$P [M+H]$^+$: 773.3. Found: 773.1. RP HPLC: R$_T$=5.89 min, 6.19 min.

(1R,3R,4R,S7)-7-(2-Cyanoethoxy (diisopropylamino)phosphinoxy)-1-(4,4'-dimethoxytrityloxymethyl)-3-(2-N-isobutyrylguanin-1-yl)-2,5-dioxabicyclo[2.2.1]heptane (2)

$^{31}$P-NMR (CDCl$_3$, 121.49 MHz): δ 150.2 (s), 149.2 (s). MS (ES): m/z calcd for C$_{45}$H$_{54}$N$_7$O$_9$P [M+H]$^+$: 868.4. Found: 868.0. RP HPLC: R$_T$=5.52 min, 5.72 min.

(1R,3R,4R,7S)-3-(4-N-Benzoyl-5-methylcytosin-1-yl)-7-(2-cyanoethoxy(diisopropylamino) phosphinoxy)-1-(4,4'-dimethoxytrityloxymethyl)-2,5-dioxabicyclo[2.2.1]heptane (3)

$^{31}$P-NMR (CDCl$_3$, 121.49 MHz): δ 150.5 (s), 150.5 (s). MS (ES): m/z calcd for C$_{48}$H$_{54}$N$_5$O$_9$P [M+H]$^+$: 876.4. Found: 876.2. RP HPLC: R$_T$=7.67 min, 8.13 min. (HPLC solvent gradient: 0.0–0.5 min 95% B, 0.5–2.0 min 95%→100% B, 2.0–7.0 min 100% B, 7.0–7.5 min 100%→95% B, 7.5–12.0 min 95% B)

(1R,3R,4R,7S)-3-(6-N-Benzoyladenin-9-yl)-7-(2-cyanoethoxy(diisopropylamino)phosphinoxy)-1-(4, 4'-dimethoxytrityloxymethyl)-2,5-dioxabicyclo [2.2.1]heptane (4)

$^{31}$P-NMR (CDCl$_3$, 121.49 MHz): δ 150.1 (s), 149.7 (s). MS (ES): m/z calcd for C$_{48}$H$_{52}$N$_7$O$_8$P [M+H]$^+$: 886.3. Found: 886.0. RP HPLC: R$_T$=6.65 min, 6.82 min.

(1R,3R,4R,S 7)-7-(2-Cyanoethoxy (diisopropylamino)phosphinoxy) -1-(4,4'-dimethoxytrityloxymethyl)-5-N-methyl-3-(thymin-1-yl)-2-oxa-5-azabicyclo[2.2.1]heptane (5)

$^{31}$P-NMR (CDCl$_3$, 121.49 MHz): δ 149.8 (s), 149.6 (s). MS (ES): m/z calcd for C$_{42}$H$_{52}$N$_5$O$_8$P [M+H]$^+$: 786.3. Found: 786.2. RP HPLC: R$_T$=5.87 min, 6.26 min.

(1S,3R,4S,7R)-7-(2-Cyanoethoxy(diisopropylamino) phosphinoxy)-1-(4,4'-dimethoxytrityloxymethyl)-3-(thymin-1-yl)-2,5-dioxabicyclo[2:2:1]heptane (6)

$^{31}$P-NMR (CDCl$_3$, 121.49 MHz): δ 150.9 (s), 150.6 (s). MS (ES): m/z calcd for C$_{41}$H$_{49}$N$_4$O$_9$P [M+H]$^+$: 773.3. Found: 773.1. RP HPLC: R$_T$=6.06 min, 6.44 min.

All documents mentioned herein are incorporated herein by reference in their entirety.

What is claimed is:

1. A method for the synthesis of an LNA phosphoramidite, the method comprising phosphitylation of the 3'-OH group of an LNA monomer with a 2-cyanoethyl-N,N,N',N'-tetraisopropylphosphoramidite in the presence of 4,5-dicyanoimidazole (DCI), wherein the molar ration between the LNA monomer and DCI is in the range from 1:07 to 1:1.

2. The method according to claim 1, which comprises at the most one precipitation step.

3. The method according to claim 1, wherein the molar ratio between the LNA monomer and 2-cyanoethyl-N,N,N',N'-tetraisopropylphosphoramidite is in the range of 1:0.9 to 1:1.

4. The method according to claim 1, wherein the phosphitylation is allowed to proceed for 0.5–4 hours.

5. The method according to claim 1, wherein the LNA monomer has a nucleobase selected from guanine, thymine, cytosine, methyl cytosine, uracil and adenine.

6. The method according to claim 1, wherein the LNA monomer is selected from oxy-β-D-ribo-LNA, thio-β-D-ribo-LNA, amino-β-D-ribo-LNA, oxy-α-L-ribo-LNA, thio-α-L-ribo-LNA and amino-α-L-ribo-LNA.

7. The method accroding to claim 1, wherein the molar ratio between the LNA monomer and DCI is 1:0.7.

* * * * *